(12) United States Patent
Jeong et al.

(10) Patent No.: US 10,010,635 B2
(45) Date of Patent: Jul. 3, 2018

(54) DETERGENT POURER STERILIZER AND STERILIZING METHOD THEREBY

(71) Applicant: Seoul Viosys Co., Ltd., Ansan-si (KR)

(72) Inventors: Jae-Hak Jeong, Seoul (KR); Sang-Cheol Shin, Suwon-si (KR); Seong-Min Lee, Seoul (KR); Ji-Won Kim, Incheon (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 14/871,954

(22) Filed: Sep. 30, 2015

(65) Prior Publication Data

US 2016/0089460 A1    Mar. 31, 2016

(30) Foreign Application Priority Data

Sep. 30, 2014 (KR) .................. 10-2014-0131980

(51) Int. Cl.
- *A61L 2/24* (2006.01)
- *A61L 2/10* (2006.01)
- *D06F 35/00* (2006.01)
- *D06F 39/02* (2006.01)

(52) U.S. Cl.
CPC ........ *A61L 2/10* (2013.01); *A61L 2/24* (2013.01); *D06F 35/008* (2013.01); *D06F 39/02* (2013.01)

(58) Field of Classification Search
CPC .............. A61L 2/10; A61L 2/24; B65D 25/40
See application file for complete search history.

(56) References Cited

U.S. PATENT DOCUMENTS

| | | | | |
|---|---|---|---|---|
| 5,487,877 A * | 1/1996 | Choi | ............ | A47K 5/00 222/192 |
| 2010/0200026 A1* | 8/2010 | Boztas | ............ | A47L 15/4242 134/115 R |
| 2011/0126370 A1* | 6/2011 | Reuben | ............ | A46B 17/06 15/167.1 |
| 2014/0166900 A1* | 6/2014 | Nelson | ............ | A61L 2/10 250/455.11 |
| 2014/0190220 A1* | 7/2014 | Lee | ............ | D06F 39/02 68/17 R |

FOREIGN PATENT DOCUMENTS

| | | |
|---|---|---|
| CN | 101535551 A | 9/2009 |
| CN | 101792966 A | 8/2010 |

OTHER PUBLICATIONS

First Office Action in Chinese Patent Application No. 201510633436.9, dated Feb. 28, 2017 (with English translation), 17 pages.
Second Office Action in Chinese Application No. 201510633436.9, dated Sep. 4, 2017.

* cited by examiner

*Primary Examiner* — Sean E Conley
(74) *Attorney, Agent, or Firm* — Perkins Coie LLP

(57) ABSTRACT

Disclosed herein is a detergent pourer sterilizer. In one aspect, a detergent pourer sterilizer is provided to include a housing including a hollow portion having an open side; a detergent pourer configured to be detachably attached to the housing; a cover member configured to open or close the one open side of the hollow portion; and at least one UV LED configured to emit ultraviolet light toward the hollow portion.

16 Claims, 2 Drawing Sheets

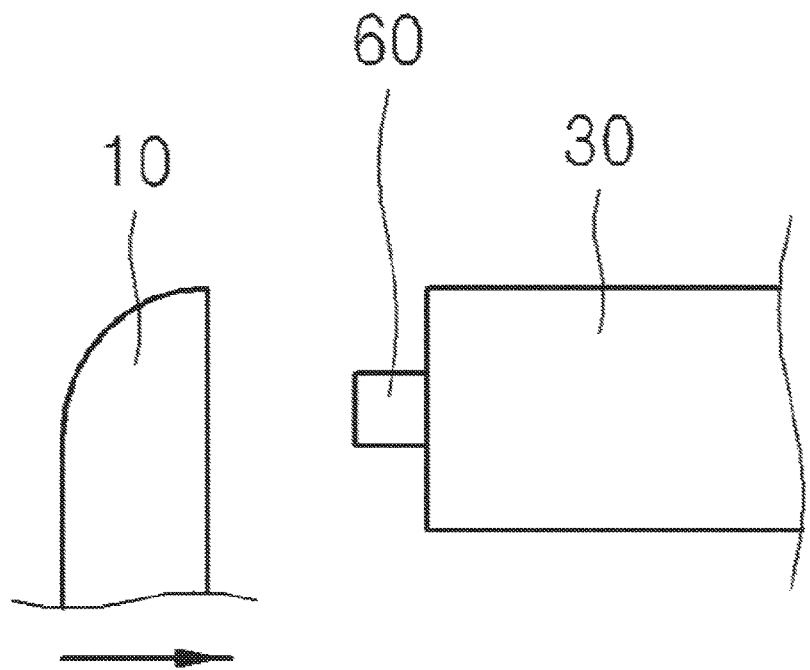

DETERGENT POURER STERILIZER AND STERILIZING METHOD THEREBY

CROSS-REFERENCE TO RELATED APPLICATIONS

This patent document claims the priority of Korean Patent Application No. 10-2014-0131980 filed on Sep. 30, 2014, in the Korean Intellectual Property Office, the disclosure of which is incorporated herein by reference.

TECHNICAL FIELD

The disclosed technology relates to a detergent pourer sterilizer. In some implementations, the disclosed technology relate to an apparatus for sterilizing a detergent introduction port of a washing machine using, for example, at least one UV LED and a method for the same.

BACKGROUND

A washing machine is provided with a detergent pourer. Water is generally sprayed into to the detergent pourer to dissolve a powder detergent or a liquid detergent. Accordingly, if the detergent pourer is not dried well after the washing operation, the detergent pourer may remain wet for a considerably long time.

SUMMARY

Various implementations of the disclosed technology provide a detergent pourer sterilizer capable of keeping the detergent pourer clean and a sterilizing method for the same.

According to an aspect of the disclosed technology, there are provided a detergent pourer sterilizer and sterilization method for performing sterilization with a UV LED installed in a detergent pourer, removing foreign substances by spraying high-pressure water, and drying the detergent pourer by injecting air.

In one aspect, a detergent pourer sterilizer is provided to include a housing including a hollow portion having an open side; a detergent pourer configured to be detachably attached to the housing; and a cover member configured to open or close the open side of the hollow portion, wherein the sterilizer includes at least one ultraviolet light emitting diode (UV LED) configured to emit ultraviolet light toward the detergent pourer being positioned in the hollow portion 20.

In some implementations, the UV LED is installed on at least one of inner surfaces of the housing to emit ultraviolet light toward the detergent pourer.

In some implementations, the UV LED is installed on an inner surface of the cover member to emit ultraviolet light toward the detergent pourer.

In some implementations, the detergent pourer sterilizer further includes power supply disposed near the housing to supply power to the UV LED, wherein electrical contacts may be installed at parts of the cover member and the housing, the parts not contacting each other when the cover member opens the hollow portion and contacting each other when the cover member closes the hollow portion, wherein the contact of the cover member may be connected to the UV LED, and the contact of the housing may be connected to the power supply, wherein the contacts of the cover member and the housing may be electrically connected to each other to supply power to the UV LED only when the cover member closes the hollow portion.

In some implementations, the UV LED may be installed on at least one of inner surfaces of the housing to emit ultraviolet light toward the detergent pourer, wherein the UV LED installed on the housing may be connected to the UV LED installed on the cover member in series.

In some implementations, the detergent pourer sterilizer further includes a switch installed at a part of the cover member, the part not contacting the housing when the cover member opens the hollow portion and contacting the housing when the cover member closes the hollow portion, wherein the switch may operate to supply power to the UV LED only when the cover member closes the hollow portion.

In some implementations, the detergent pourer sterilizer further includes a nozzle installed on the housing for spraying high-pressure water toward the detergent pourer.

In some implementations, the housing includes an air injection hole for injecting air toward the hollow portion therethrough and an air discharge hole for discharging the injected air.

In some implementations, the detergent pourer sterilizer further comprises a water discharge hole formed in the housing and operating as the air discharge hole.

In some implementations, the detergent pourer includes a material allowing ultraviolet light to be transmitted therethrough.

In some implementations, the detergent pourer or the housing has at least one region of an inner surface coated with $TiO_2$ such that $TiO_2$ causes photocatalytic reaction with ultraviolet light.

In some implementations, the detergent pourer sterilizer further includes a reflector installed on an inner surface of the housing.

In some implementations, the detergent pourer sterilizer further includes an alarm means to alarm an open state of the cover member when the cover member is opened as power is supplied to the UV LED.

In another aspect, there is provided a method for sterilizing a detergent pourer of a washing machine including a housing including a hollow portion having an open side, a detergent pourer configured to detachably attached to the housing, and a cover member configured to open or close the open side of the hollow portion, and a ultraviolet light emitting diode (UV LED) configured to emit ultraviolet light toward the hollow portion, the method including starting sterilizing of the detergent pourer when operation of the washing machine is completed or an instruction from a user to start the sterilization is received, wherein the sterilizing of the detergent pourer includes checking if there is no laundry in a washing tub; and supplying power to the UV LED and turning on the UV LED only when the cover member is closed after checking that there is no laundry in the washing tub.

In some implementations, the housing includes a nozzle for spraying high-pressure water toward the detergent pourer, wherein the sterilizing of the detergent pourer further includes spraying the high-pressure water the washing tub only when the cover member is closed after checking that there is no laundry in the washing tub, wherein the spraying is performed before the turning on of the UV LED is performed.

In some implementations, the housing includes an air injection hole for injecting air toward the hollow portion and an air discharge hole for discharging the injected air, wherein the sterilizing of the detergent pourer further includes injecting the air only when the cover member is closed after checking that there is no laundry in the washing tub, wherein the injecting of the air is performed before the turning on of the UV LED is performed.

In some implementations, the housing includes an air injection hole for injecting air toward the hollow portion and an air discharge hole for discharging the injected air, wherein the sterilizing of the detergent pourer further includes injecting the air only when the cover member is closed after checking that there is no laundry in the washing tub, wherein the injecting of the air is performed after the spraying of the high-pressure water is performed and before the turning on of the UV LED is performed.

In some implementations, the sterilizing of the detergent pourer is stopped when the cover member is opened after checking that there is no laundry in the washing tub.

In some implementations, when sterilizing of the detergent pourer is stopped, an alarm is triggered.

In some implementations, the sterilizing of the detergent pourer starts automatically only when an accumulated number of uses of the washing machine after a most recent execution of the sterilizing is greater than or equal to 2.

In some implementations, the sterilizing is signaled when the sterilizing is being performed, and completion of the sterilizing is signaled when the sterilizing is completed.

According to the disclosed technology, a detergent pourer can be kept clean all the time. Thereby, a washing tub may be prevented from being contaminated, causing a user to inconveniently clean the detergent pourer or leaving the detergent pourer open maybe lowered.

It should be noted that effects of the disclosed technology are not limited to those described above and other effects of the disclosed technology will be apparent to those skilled in the art from the following descriptions taken in conjunction with the accompanying drawings.

BRIEF DESCRIPTION OF THE DRAWINGS

FIG. 2 is an enlarged view illustrating a switch installed between the detergent pourer and the housing shown in FIG. 1.

DETAILED DESCRIPTION

Figure 1:
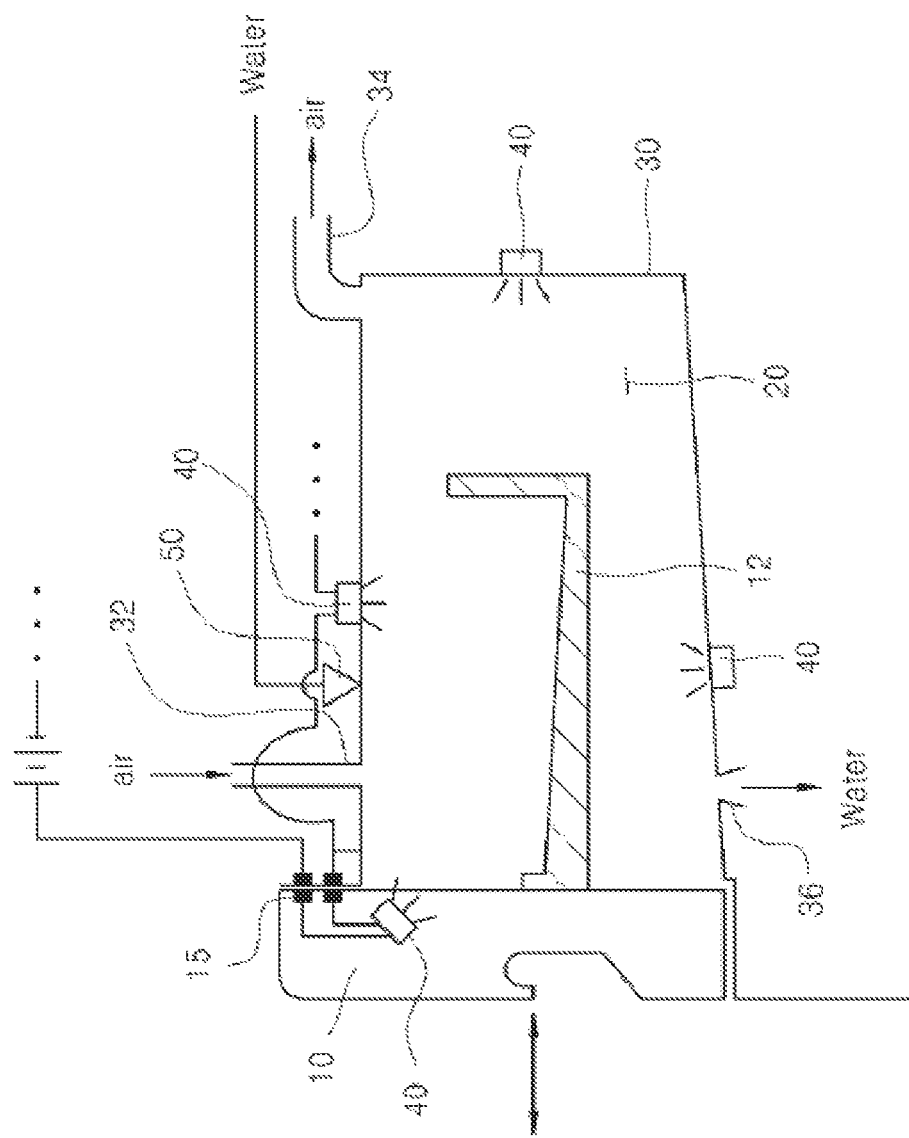
FIG. 1 is a lateral cross-sectional view illustrating a detergent pourer sterilizer according to an embodiment of the disclosed technology.

When a detergent pourer is left wet and closed for a long time, germs or mold easily reproduces . Moreover, a lot of slime forms, and thus the detergent pourer becomes dirtier. This requires the user to periodically clean the detergent pourer, thereby causing significant inconvenience to the user. In addition, if the detergent pourer is contaminated, germs or mold enter a washing tub when the detergent flows into the washing machine along with water, which is one of causes of contamination of the washing tub.

For this reason, users of the washing machine generally leave the detergent pourer open after using the washing machine such that the detergent pourer is dried. However, this merely slows down the reproduction rate of germs or mold, and cannot suppress reproduction of the germs or mold. Furthermore, if the detergent pourer is kept open, the detergent pourer is not good to view and dust, which is another cause of contamination, may collect on the detergent pourer.

Under the recognition the problems above, the disclosed technology provide a detergent pourer sterilizer capable of keeping the detergent pourer clean and a sterilizing method for the same.

The disclosed technology is not limited to exemplary embodiments disclosed herein but may be implemented in various different forms.

In the description given below, it is apparent to those skilled in the art that a structure or constituent of one embodiment may be applied to or replaced with a structure or constituent of another embodiment or omitted, or another constituent may be added thereto, if necessary.

Hereinafter, preferred embodiments of the disclosed technology will be described in detail with reference to the accompanying drawings.

FIG. 1 is a lateral cross-sectional view illustrating a detergent pourer sterilizer according to an embodiment of the disclosed technology; and FIG. 2 is an enlarged view illustrating a switch installed between the detergent pourer and the housing shown in FIG. 1.

Structure of Detergent Pourer

As shown in FIG. 1, a washing machine includes a hollow portion 20 which has a hollow inner part and is formed in a certain upper region of a housing 30 at which a washing tub installed. A detergent pourer 12 is positioned in the hollow portion. The detergent pourer 12 defines a space in which the user puts a detergent. When the user puts the detergent in the detergent pourer 12, the detergent stays in the detergent pourer 12.

According to one embodiment of the disclosed technology, the detergent pourer 12 is integrated with a cover member 10 and behaves together with the cover member 10. Accordingly, the user withdraws the detergent pourer 12 out by pulling the cover member 10 in the direction indicated by an arrow in FIG. 1, puts a detergent therein, and then pushes the cover member 10 back to put the detergent pourer 12 in the hollow portion 20 and begin washing the laundry.

However, the detergent pourer 12 does not need to be integrated with the cover member 10. The cover member 10 may rotate about an axis to open and close like a hinged door, and the detergent pourer 12 may be withdrawn out in a sliding manner or another manner in connection with rotation of the cover member 10. Alternatively, the detergent pourer 12 may be provided and behave separately from the cover member 10. Additionally, the detergent pourer 12 may be fixed.

According to an embodiment of the disclosed technology, one side of the hollow portion is open, and the detergent pourer is configured to move back and forth through this side. However, it is apparent that embodiments of the disclosed technology are not limited to this structure.

Installation Structure of UV LED

In the disclosed technology, a UV LED 40 may be installed on the inner surface of the housing 30. The UV LED is installed to emit ultraviolet light toward the hollow portion 20, more specifically, toward the detergent pourer 12. As shown in the figure, a plurality of UV LEDs are appropriately installed on the upper surface, lateral surface, and lower surface of the housing 30 to emit ultraviolet light onto all surfaces of the detergent pourer 12.

In addition, a UV LED may be installed on the cover member 10. The UV LED is installed to emit ultraviolet light toward the hollow portion 20, more specifically, toward the detergent pourer 12.

The power supply to supply power to the UV LED is installed near the housing. Accordingly, to supply power to the UV LED installed on the cover member 10, an electrical connection is needed between the cover member 10 and the housing 30, which make relative movement with respect to each other. Meanwhile, ultraviolet light emitted from the UV LED is hazardous to the human body, and thus it is desired that ultraviolet light does not leak outside.

Therefore, in the disclosed technology, power is allowed to be supplied to the UV LED only when the cover member 10 close one open side of the hollow portion 20, and is not allowed to be supplied to the UV LED when the cover member 10 opens the hollow portion 20. To this end, according to an embodiment of the disclosed technology, electrical contacts 15 are installed at parts of the cover member 10 and the housing 30 where the cover member 10 does not contact the housing 30 when the hollow portion 20 is open and contacts the housing 30 when the hollow portion 20 is closed by the cover member 10. Thereby, the contacts of the cover member 10 and the housing 30 are electrically connected to each other only when the cover member 10 closes the hollow portion 20. In addition, the contact of the cover member 10 is configured to be connected to the UV LED 40 installed on the cover member 10, and the contact of the housing 30 is connected to the power supply. Accordingly, according to one embodiment of the disclosed technology, power can be supplied to the UE LED only when the cover member 10 is positioned to close the hollow portion 20.

Additionally, as shown in the figure, if the UV LEDs installed on the cover member 10 and the housing 30 are connected in series, the UV LEDs may be electrically disconnected from the power supply and thus may not be turned on when the cover member 10 is positioned not to close the hollow portion 20.

However, embodiments of the disclosed technology are not limited thereto. A flexible PCB may be used to keep the UV LED of the cover member 10 electrically connected to the power supply between the cover member 10 and the housing 30, and a separate means may be used so as not to supply power to the UV LED when the cover member 10 is closed or open.

That is, as shown in FIG. 2, a switch 60 may be installed at the hollow portion 20 such that the switch 60 installed at the housing 30 is pressed only when the cover member 10 closes the hollow portion, and power may be supplied to the UV LED only when the switch 60 is pressed.

It is also possible to employ both the switch and the contacts.

Emission of Ultraviolet Light and Corresponding Sterilizing Structure

An optical part for adjusting the dispersion angle of ultraviolet light may be installed at the UV LED, and a cover roughened through, for example, a sandblast process may be installed to make the ultraviolet light a surface light source.

Meanwhile, if the detergent pourer 12 described above is formed of a material allowing ultraviolet light to be transmitted therethrough, ultraviolet light may reach all the surface of the detergent pourer 12 such that there is no shaded area on the detergent pourer 12. Thereby, ultraviolet light emitted onto the detergent pouring port may reach the inner surface of the housing positioned on the opposite side, sterilizing the inner surface of the housing. As such material, PMMA having a relatively high proportion of monomer may be used. Such material has a high transmissivity for ultraviolet light, and is not easily discolored.

Meanwhile, photocatalytic material coating such as $TiO_2$ may be applied to the detergent pourer such that photocatalytic reaction occurs. When ultraviolet light having a wavelength near 275 nm, which has a sterilization effect, causes $TiO_2$ to produce the photocatalytic reaction, better deodorization and anti-bacterial effects may be obtained, thereby suppressing reproduction of mold and more securely preventing reproduction of germs.

$TiO_2$ coating maybe applied not only to the detergent pourer but also to the inner surface of the housing such that photocatalytic reaction occurs. In particular, a better effect may be obtained when the detergent pourer is formed of a material allowing ultraviolet light to be transmitted therethrough.

If a reflector is installed on the inner surface of the housing, the sterilization effect according to ultraviolet light is further enhanced. The reflector improves the sterilization efficiency when a closed space is sterilized by emitting ultraviolet light.

Spray Nozzle

According to the disclosed technology, various other structures are provided as well as ultraviolet light structure for sterilization.

According to one embodiment of the disclosed technology, a nozzle 50 may be installed at the upper portion of the housing to spray high-pressure water toward the detergent pourer 12. Such spray nozzle may be provided separately from a nozzle for spraying water into the detergent pourer 12 in order to dissolve the detergent and introduce the same into the washing tub. On the other hand, one common nozzle may be used with different pressures.

When the inner surface of the housing including the detergent pourer 12 are washed, water is sprayed with a higher pressure than when the detergent is poured, in order to wash off residues stuck to, for example, the surface of the detergent pourer. The residues washed off the surface are discharged through a water discharge hole 36.

Preferably, the nozzle is directly connected to a water pipe such that water is sprayed with the water pressure from the water pipe. However, embodiments of the disclosed technology are not limited thereto.

Ventilation Structure

Next, according to the disclosed technology, air is allowed to flow through the hollow portion such that water or moisture in the hollow portion is quickly removed.

Referring to FIG. 1, an air injection hole 32 and an air discharge hole 34 are arranged at proper positions on the upper portion of the housing 30 in proper directions, such that the injected air causes a turbulent flow, quickly evaporating water on the surface or pushing the water toward the water discharge hole 36.

While the air discharge hole 34 and the water discharge hole 36 are illustrated as being separately provided in FIG. 1, the water discharge hole may perform the function of the air discharge hole without provided a separate air discharge hole, which may be advantageous in drying the washing tub as air is allowed to enter the washing tub.

Sterilization

Hereinafter, the sterilization operation of the detergent pourer sterilizer of the disclosed technology will be described.

The sterilizer according to the disclosed technology may automatically operate or be manually operated by the user, when necessary, or may be configured such that the two aforementioned methods are applicable. If the sterilizer is configured to automatically operate, sterilization maybe performed every time the washing operation is completed or maybe performed periodically, for example, once per every three washing operations or intermittently.

Alternatively, sterilization may automatically begin only when the washing machine is used more than equal to a plurality of times, e.g., three times after the latest sterilization operation.

Such sterilization operation of the detergent pourer begins when operation of the washing machine is completed or the user begins the sterilization operation by pressing a button on the washing machine.

Once the sterilization operation begins, it is checked whether the cover member 10 is closed or not. If the cover member is opened, the sterilization operation is immediately stopped. The closed state of the cover member may be checked by, for example, checking if the switch 60 remains pressed down. Meanwhile, if the sterilization operation is stopped, an alarm is signaled to inform the user that the sterilization operation has been stopped. The alarm may be signaled by sound or display.

At the stage at which the sterilization operation begins, it is checked whether there is no laundry in the washing tub. Whether there is no laundry in the washing tub may be determined by weight of the washing tub, the number of times of opening and closing of the door of the washing tub after washing or the time at which the door is opened and closed.

After it is determined that there is no laundry in the washing tub, water is sprayed with a high pressure through the nozzle 50 for a certain time to clearly remove residues stuck to the detergent pourer or the inner surface of the housing. The sprayed water is discharged through the water discharge hole 36.

Next, air is injected through the air injection hole 32 with a high pressure to discharge residual water from the detergent pourer or the housing through the air discharge hole 34 or the water discharge hole 36 and to dry the detergent pourer or the housing.

Next, power is applied to the UV LED 40 to keep the UV LED 40 turned on for more than a certain time. Thereby, ultraviolet light is uniformly emitted onto the inner surface of the housing or the detergent pourer, performing sterilization.

By emitting ultraviolet light after the detergent pourer is washed with water and dried, the sterilization operation is finished.

Meanwhile, if there is no indication for the sterilization operation, the user may accidentally open the cover member during the sterilization. Accordingly, it is preferably to signal the sterilization operation when the sterilization operation is performed and to signal completion of the sterilization operation when the sterilization operation is completed.

It is apparent to those skilled in the art that the disclosed technology is not limited to the embodiments and drawings disclosed in this specification, and modifications and variations can be made thereto without departing from the technical idea of the disclosed technology.

What is claimed is:

1. A detergent pourer sterilizer including:
a housing having an opening on one side of the housing, the opening providing a hollow portion inside the housing;
a detergent pourer detachably attached to the housing; and
a cover member moveably connected to the housing to open or close the opening of the hollow portion, the movement of the cover member changing a position of the detergent pourer in the housing,
a first ultraviolet light emitting diode (UV LED) located on an upper portion of the housing and configured to emit ultraviolet light toward the detergent pourer positioned in the hollow portion, the first UVLED electrically connected with a power supply through a first electrical contact disposed in the housing; and
a second UVLED located on the cover member and configured to emit ultraviolet light toward the detergent pourer position in the hollow portion, the second UVLED being supplied with power through a second electrical contact disposed in the cover member,
wherein the first electrical contact and the second electrical contact are positioned to electrically connect to each other when the cover member closes the opening of the hollow portion.

2. The detergent pourer sterilizer according to claim 1, wherein the UV LED is installed on at least one of inner surfaces of the housing to emit ultraviolet light toward the detergent pourer.

3. The detergent pourer sterilizer according to claim 1, wherein the UV LED is installed on an inner surface of the cover member to emit ultraviolet light toward the detergent pourer.

4. The detergent pourer sterilizer according to claim 1, further comprising an additional UV LED installed on the housing to emit ultraviolet light toward the detergent pourer, wherein the additional UV LED installed on the housing is connected to the UV LED installed on the cover member in series.

5. The detergent pourer sterilizer according to claim 1, further comprising: a switch installed at a part of the cover member, the part not contacting the housing when the cover member opens the hollow portion and contacting the housing when the cover member closes the hollow portion, wherein the switch operates to supply power to the UV LED only when the cover member closes the hollow portion.

6. The detergent pourer sterilizer according to claim 1, wherein the housing comprises an air injection hole for injecting air toward the hollow portion therethrough and an air discharge hole for discharging the injected air.

7. The detergent pourer sterilizer according to claim 6, further comprising: a water discharge hole formed in the housing and operating as the air discharge hole.

8. The detergent pourer sterilizer according to claim 1, wherein the detergent pourer includes a material allowing ultraviolet light to be transmitted therethrough.

9. The detergent pourer sterilizer according to claim 1, wherein the detergent pourer or the housing has at least one region of an inner surface coated with photocatalytic material such that photocatalytic material causes photocatalytic reaction with ultraviolet light.

10. The detergent pourer sterilizer according to claim 1, further comprising: a reflector installed on an inner surface of the housing.

11. The detergent pourer sterilizer according to claim 1, further comprising an alarm means to alarm an open state of the cover member when the cover member is opened as power is supplied to the UV LED.

12. The detergent pourer sterilizer according to claim 1, wherein each of the first electrical contact and the second electrical contact includes two contact points and the two contact points of the first electrical contact are electrically connected with the two contact points of the second electrical contact, respectively, when the cover member closes the opening of the hollow portion.

13. A detergent pourer sterilizer including:
a housing having an open side and provide a hollow portion therein, the housing having a top surface, a bottom surface and a side surface connecting the top surface and the bottom surface and facing the open side;
a detergent pourer configured to be detachably attached to the housing;

a cover member disposed on the open side of the housing and configured to open or close the open side of the housing, the cover member movably connected to the housing along a direction parallel to the housing;

a nozzle installed on the housing for spraying high-pressure water toward the detergent pourer;

at least one ultraviolet light emitting diode (UV LED) positioned on the top surface of the housing and configured to emit ultraviolet light from the top surface of the housing toward the detergent pourer positioned in the hollow portion; and an air injection hole located on the top surface of the housing and injecting air toward the hollow portion of the housing.

14. The detergent pourer sterilizer according to claim 13, wherein the nozzle installed over the upper portion of the housing.

15. The detergent pourer sterilizer according to claim 13, further comprising an additional nozzle to configure spraying water into the detergent pourer.

16. The detergent pourer sterilizer according to claim 13, wherein the nozzle is connected to a water pipe.

* * * * *